United States Patent [19]

Scopelianos et al.

[11] Patent Number: 5,824,333

[45] Date of Patent: Oct. 20, 1998

[54] INJECTABLE LIQUID COPOLYMERS FOR SOFT TISSUE REPAIR AND AUGMENTATION

[75] Inventors: Angelo G. Scopelianos; Rao S. Bezwada, both of Whitehouse Station; Steven C. Arnold, Sparta, all of N.J.

[73] Assignee: Ethicon, Inc., Somerville, N.J.

[21] Appl. No.: 746,180

[22] Filed: Nov. 6, 1996

Related U.S. Application Data

[63] Continuation of Ser. No. 324,952, Oct. 18, 1994.

[51] Int. Cl.$^6$ .............................. A61F 2/02; A61F 2/08; A61K 31/765; C08G 63/91
[52] U.S. Cl. ...................... 424/423; 424/78.37; 525/408; 525/413; 525/415; 525/450; 528/352; 528/361; 604/93; 623/13; 623/14
[58] Field of Search ................................ 424/78.37, 423; 525/408, 413, 415, 450; 528/352, 361; 604/93; 623/13, 14

[56] References Cited

U.S. PATENT DOCUMENTS

| | | | |
|---|---|---|---|
| 4,595,713 | 6/1986 | St. John | 523/105 |
| 4,664,655 | 5/1987 | Orentreich et al. | 604/232 |
| 4,758,234 | 7/1988 | Orentreich et al. | 604/232 |
| 4,803,075 | 2/1989 | Wallace et al. | 424/423 |
| 4,938,763 | 7/1990 | Dunn et al. | 604/891.1 |
| 5,204,382 | 4/1993 | Wallace et al. | 523/115 |
| 5,278,201 | 1/1994 | Dunn et al. | 523/113 |
| 5,278,202 | 1/1994 | Dunn et al. | 523/113 |
| 5,442,033 | 8/1995 | Bezwada | 528/354 |

FOREIGN PATENT DOCUMENTS

| | | |
|---|---|---|
| 0 270 987 A2 | 12/1987 | European Pat. Off. . |
| 0 427 185 A3 | 11/1990 | European Pat. Off. . |
| 42 35 312.2 | 4/1993 | Germany . |
| WO 94/02184 | 2/1994 | WIPO . |

OTHER PUBLICATIONS

J. of Urology, vol. 151, May 1994, Number 5 Injectable Teflon Paste for Female Stress Incontinence: Long term Follow–up and Results; J. F. Buckley, et al. J. F. Buckley, et al.

Neurourology and Urodynamics 12:131–137 (1993) Complications of Teflon Injection for Stress Urinary Incontinence. Pentti, et al.; 1993 Wiley–Liss, inc.

J. of Urology vol. 142, 821–822, Pulmonary Migration Following Perurethral Polytetrafluoroethylene Injection for Urinary Incontinence. H. Claes, et al.

Plastic & Reconstructive Surgery—Apr. 1991, vol. 87, 693–702, Bioplastique: A New Textured Copolymer Microparticle Promise Permanence in Soft–Tissue Augmentation. Robert A. Ersek, M.D., et al.

J. of Urology vol. 148, 1797–1800, Dec. '92, Early Experimence with Intrauuethral Collagen Injections for urinary Incontinence. Sender Herschorn, et al.

JAMA Jun. 22/29, 1984–vol. 251, No. 24 3277–3281, Clinical Investigation: Migration and Granulomatous Reactino After Periurethral Injection of Polytef (Teflone). Anthont A. Malizia, Jr. M.D., et al.

Anthont A. Malizia, Jr. M.D., et al.

J. of Endourology vol. 6, No. 3, '92, 275–277, Endourologic Control of Incontinence with GAX Collagne: The LSU Experinece. Rodney A. Appell, M.D., et al.

J. American Acad. Dermatol. Dermatologic Surgery; No. 5, Nov. 1989, 992–998, Dermal Implants: Safety of Products Injected for Soft Tissue Augmentation. David P. Clark, et al.

Dermatologic Clinics, vol. 11—No. 2, Apr. '93, 361–367, Dermal Filler Materials Melvin L. Elson, M.D.

J. Dermatol. Surg. Oncol. 14:7 Jul. 1988, 66–75, Comparison of Injectable Silicone Versus Collagen for Soft Tissue Augmentation. Kevin A. Shumrick, M.D., et al.

Clinics in Plastic Surgery vol. 18, No. 4, Oct. '91, 829–855, Alloplastic Implants for Men Brian H. Novack, M.D.

Donaldson, Lufkin & Jenrett Research Bulletin, Oct. 6, 1993, 1565–93 Kent Blair.

Aesthetic Plastic Surgery, 16:59–65, 1992, Bioplastique: A New Biphasic Polymer for Minimally Invasive Injection Implantation.

Robert A. Ersek, M.D., et al.

Buckley et al., J. Urology, vol. 151(5):764, May 1994.

Kiilholma et al., Neurourology and Urodynamics, vol. 12:131–137, 1993.

Stroobants et al., J. Urology, vol. 142:821–822, 1989.

Ersek et al., Plastic and Reconstructive Surgery, vol. 87(4), pp. 693–702, Apr. 1991.

Herschorn et al., J. Urology, vol. 148, pp. 1797–1880, Dec. 1992.

Malizia et al., JAMA, vol. 251, pp. 3277–3281, 1984.

Appell et al., J. Endourology, vol. 6(3), pp.275–277, 1992.

(List continued on next page.)

*Primary Examiner*—Carlos A. Azpuru
*Attorney, Agent, or Firm*—Hal Brent Woodrow

[57] ABSTRACT

The present invention provides injectable, bioabsorbable liquid copolymers suitable for use as a soft tissue repair or augmentation material in animals comprising a liquid polymer selected from the group consisting of liquid polymers of a plurality of at least two different first lactone repeating units and liquid polymers of a plurality of first lactone and second lactone repeating units; wherein the first lactone repeating units are selected from the group consisting of ε-caprolactone repeating units, trimethylene carbonate repeating units, ether lactone repeating units (which for the purpose of this invention shall mean 1,4-dioxepan-2-one and 1,5-dioxepan-2-one) and combinations thereof and the second lactone repeating units are selected from the group consisting of glycolide repeating units, lactide repeating units (which for the purpose of this invention are defined to be L-lactide, D-lactide, or D,L-lactide repeating units), p-dioxanone repeating units and combinations thereof. Additionally, the present invention also discloses methods of using these liquid copolymers for tissue augmentation and repair as well as kits which include prefilled containers to facilitate the use of these materials.

20 Claims, No Drawings

OTHER PUBLICATIONS

Clark et al., J. Am. Acad. Dermatol., vol. 21 (Part 1), pp. 992–998, Nov. 1989.

Elson, Current Therapy, vol. 11(2), pp. 361–367, Apr. 1993.

Shumrick et al., J. Dermatol. Surg. Onocl., vol. 14(7), pp.66–75, Jul. 1988.

Novack, Clinics in Plastic Surgery, vol. 18(4), pp. 829–855, Oct. 1991.

Research Bulletin, #1565–93, Donaldson, Lufkin & Jeanrette Securities Corporation, Oct. 6, 1993.

Ersek et al., Aesthetic Plastic Surgery, vol. 16, pp. 59–65, 1992.

ically no
INJECTABLE LIQUID COPOLYMERS FOR SOFT TISSUE REPAIR AND AUGMENTATION This is a continuation of application Ser. No. 08/324,952, filed Oct. 18, 1994, now abandoned.

FIELD OF THE INVENTION

The present invention relates to liquid polymers that are suitable for use in soft tissue repair and augmentation. More specifically, the present invention provides biocompatible, bioabsorbable, injectable, liquid copolymers that are suitable for soft tissue repair and augmentation.

BACKGROUND OF THE INVENTION

The repair or augmentation of soft tissue defects or contour abnormalities caused by facial defects, acne, surgical scarring or aging has proven to be very difficult. A number of materials have been used to correct soft tissue defects with varying degrees of success, but currently no material appears to be completely safe and effective. In the past, small amounts of liquid silicone were used to correct minor soft tissue defects where minimal mechanical stress was present at the recipient site. Unfortunately, liquid silicone from these injections appears to migrate to distant body parts and causes a variety of physiological and clinical problems. In response to these problems and the misuse of liquid silicone, the FDA has prohibited the use of liquid silicone in humans.

In the 1970's, reconstituted injectable bovine collagen became available and appeared to be an effective treatment for soft tissue defects. However, over time, the benefits of the collagen treatment have proven to be short-lived; the collagen reabsorbs in two to three months. Additionally, safety measures must be employed with this material to avoid allergic reactions to the bovine proteins in the collagen. To solve these shortcomings, crosslinked collagen has been introduced to extend the effect of treatments to approximately six (6) months. However, allergic reactions still occur with the crosslinked collagen material and frequent readministration of the crosslinked material is still required.

Recently, several authors have described new materials that may be used for soft tissue repair or augmentation such as biocompatible ceramic particles in aqueous gels, thermoplastic materials, thermosetting materials and lactic acid based polymer blends that avoid some of the problems previously experienced with collagen and liquid silicone.

Injectable implants of biocompatible ceramic particles in aqueous gels were first proposed by Wallace et al. in U.S. Pat. No. 5,204,382. The implants consisted of ceramic particles of calcium phosphate from a nonbiological source, mixed with an aqueous gel carrier in a viscous polymer (such as polyethylene glycol, hyaluronic acid, poly (hydroxyethyl methacrylate) and collagen). Although these materials are generally nontoxic, there appears to be risks associated with the use of nonabsorbable particulate materials related to the migration of these particles to distance sites in the body.

Thermoplastic and thermosetting defect fillers were originally described by Dunn et al. in U.S. Pat. Nos. 4,938,763, 5,278,201 and 5,278,202. In these patents, Dunn proposes the use of both a thermoplastic material with a solvent and a thermosetting material with a curing agent to form solid implants in situ. Although the biodegradable materials Dunn suggests for use as thermoplastics appear acceptable, the solvents necessary to dissolve them for injection into tissue appear to be less than acceptable. Additionally, Dunn's thermoplastic and thermosetting materials have limited utility in filling soft tissue because they solidify. Similar commercially available materials exhibit ultimate yield stresses of approximately 10,000 psi; in comparison, human skin exhibits ultimate yield stresses of from 500 to 2,000 psi. Therefore, due to palpability concerns, the thermoplastic and thermosetting materials that Dunn proposed appear to be too hard for use in soft tissue augmentation or repair and especially in dermal augmentation or repair.

Soft tissue repair or augmentation has also been proposed using lactic acid based polymer blends of amorphous oligomers with crystalline oligomers or polymers (Buchholz et al. 4,235,312 A1). Buchholz's blends were developed to provide a pasty to waxy material which could be used as an absorbable implant to replace the brittle copolymers of lactic acid and glycolic acid already described for use as bone waxes. However, these blends do not appear to be suitable for use as injectable soft tissue defect fillers, because they are too viscous to be injected through a needle which significantly limits the utility of these blends. Furthermore, the low molecular weight liquid oligomers described by Buchholz are slightly soluble in body fluids, which means that these oligomers will quickly diffuse out of the site of implantation to other areas of the body.

In view of the deficiencies of the soft tissue augmentation materials previously considered, it is evident that new soft tissue augmentation materials need to be developed. Ideally, any new augmentation material would have several important characteristics not possessed by any one of the previously discussed materials. For example, any new augmentation material should be completely bioabsorbable to avoid the possibility of long term chronic irritation of tissues or migration of nonabsorbable materials over time to different areas of the body. The new augmentation materials should also provide soft tissue augmentation for at least six months to avoid frequent readministration of the augmentation material. Furthermore, new soft tissue augmentation materials should be easy to administer preferably by injection. Finally, the ideal soft tissue augmentation material would have the appropriate degree of pliability for the tissue into which the new material was being implanted to provide life like tissue augmentation. As discussed above, none of the currently available materials have all of these characteristics.

Therefore, it is an object of the present invention to provide a safe, injectable, long lasting, bioabsorbable, soft tissue repair and augmentation material.

SUMMARY OF THE INVENTION

The present invention provides injectable, bioabsorbable liquid polymers suitable for use as a soft tissue repair or augmentation material in animals comprising a liquid polymer selected from the group consisting of liquid polymers of at least two first repeating units and liquid polymers of a plurality of first lactone and second lactone repeating units; wherein the first lactone repeating units are selected from the group consisting of ε-caprolactone repeating units, trimethylene carbonate repeating units, ether lactone repeating units (which for the purpose of this invention shall mean 1,4-dioxepan-2-one and 1,5-dioxepan-2-one) and combinations thereof and the second lactone repeating units are selected from the group consisting of glycolide repeating units, lactide repeating units (which for the purpose of this invention are defined to be L-lactide, D-lactide, or D,L-lactide repeating units), p-dioxanone repeating units and combinations thereof.

In another embodiment of the present invention, there is also provided a prefilled pharmaceutical container having an injectable, bioabsorbable, liquid polymer loaded therein, comprising: a) a liquid polymer selected from the group consisting of liquid polymers of at least two first lactone repeating units and liquid polymers of a plurality of first lactone and second lactone repeating units; wherein the first lactone repeating units are selected from the group consisting of ε-caprolactone repeating units, trimethylene carbonate repeating units, ether lactone repeating units and combinations thereof and the second lactone repeating units are selected from the group consisting of glycolide repeating units, lactide repeating units, p-dioxanone repeating units and combinations thereof; and b) a container for storing said liquid polymers, said container having a cylindrical storage area and an outlet and an end to said cylindrical storage area, the outlet having a removable sterile seal, the end having a movable sterile seal which may be advanced into said cylindrical storage area.

In yet another embodiment of the present invention, there is also provided a pharmaceutical kit suitable for administering an injectable, bioabsorbable liquid polymers comprising: a) a liquid polymer selected from the group consisting of liquid polymers of at least two first lactone repeating units and liquid polymers of a plurality of first lactone and second lactone repeating units; wherein the first lactone repeating units are selected from the group consisting of ε-caprolactone repeating units, trimethylene carbonate repeating units, ether lactone repeating units and combinations thereof and the second lactone repeating units are selected from the group consisting of glycolide repeating units, lactide repeating units, p-dioxanone repeating units and combinations thereof; and b) a device containing said liquid polymers, said device having an outlet for said liquid polymers, an ejector for expelling the liquid polymers through the outlet and a hollow tubular member fitted to the outlet for administering the liquid polymers into a site within the body.

In a further embodiment of the present invention there is also provided a method for repairing or augmenting soft tissue in animals comprising: a) selecting the animal soft tissue to be repaired or augmented; and b) placing an injectable, bioabsorbable liquid polymer suitable for use as a soft tissue repair augmentation material composed of a liquid polymer selected from the group consisting of liquid polymers of at least two first lactone repeating units and liquid polymers of a plurality of first lactone and second lactone repeating units; wherein the first lactone repeating units are selected from the group consisting of ε-caprolactone repeating units, trimethylene carbonate repeating units, ether lactone repeating units and combinations thereof and the second lactone repeating units are selected from the group consisting of glycolide repeating units, lactide repeating units, p-dioxanone repeating units and combinations thereof; into the animal soft tissue.

DETAILED DESCRIPTION OF THE INVENTION

We have surprisingly discovered that by selecting appropriate combinations of monomers that bioabsorbable liquids may be formed that are suitable for use in soft tissue repair and augmentation. These bioabsorbable liquid polymers have remarkably low viscosities which enable the material to be injected into soft tissue with a syringe and needle without heating or solvents. Additionally, these liquid polymers, unlike materials which harden after implantation, are suitable for restoring dermal tissue with the pliability similar to natural tissue.

These liquid polymers may be administered anywhere in the body of animals where a bulking agent is needed (e.g., intradermally, subcutaneously, intramuscularly and submucosally) in a therapeutic amount to provide the desired cosmetic or prosthetic effect. These liquid polymers may be used in humans and a variety of animals including domestic animals such as dogs, cats, cattle, sheep, horses and primates.

Suitable nontoxic bioabsorbable copolymers and terpolymers, that are fluids at body temperature, may be used as the injectable liquid polymer. These polymers are characteristically noncrystalline polymers with glass transition temperatures of 10° C. or less. In particular, these liquid copolymers are composed of in the range of from about 65 mole percent to about 35 mole percent of ε-caprolactone, trimethylene carbonate, ether lactone (which for the purpose of this invention is defined to be 1,4-dioxepan-2-one and 1,5-dioxepan-2-one) repeating units or combinations thereof with the remainder of the polymer being second lactone repeating units produced by a monomer selected from the group consisting of glycolide, lactide (which for the purpose of this invention also includes D-lactide, L-lactide and D,L-lactide), p-dioxanone and combinations thereof. Additionally, ε-caprolactone, trimethylene carbonate, or an ether lactone may be copolymerized to provide a noncrystalline liquid copolymer. Preferred are liquid copolymers composed of in the range of from about 65 mole percent to about 35 mole percent ε-caprolactone or an ether lactone repeating units with the remainder of the copolymer being trimethylene carbonate repeating units. The liquid polymers may be linear, branched, or star branched; statistically random copolymers, terpolymers, or the like; amorphous block copolymers, terpolymers, or the like. Examples of suitable terpolymers are terpolymers selected from the group consisting of poly (glycolide-co-ε-caprolactone-co-p-dioxanone) and poly(lactide-co-ε-caprolactone-co-p-dioxanone) wherein the mole percent of ε-caprolactone repeating units is from about 35 to about 65 mole percent. Preferred are terpolymers having in the range of from 40 to 60 mole percent of ε-caprolactone repeating units. These polymers will also be purified to substantially remove unreacted monomers which may cause an inflammatory reaction in tissue.

Most preferred are liquid polymers selected from the group consisting of poly(ε-caprolactone-co-trimethylene carbonate), poly(lactide-co-trimethylene carbonate), poly(ε-caprolactone-co-p-dioxanone), poly(trimethylene carbonate-co-p-dioxanone), poly(ε-caprolactone-co-lactide), poly(lactide-co-1,5-dioxepan-2-one), poly(1,5-dioxepan-2-one-co-p-dioxanone), poly(lactide-co-1,4-dioxepan-2-one), and poly(1,4-dioxepan-2-one-co-p-dioxanone). The mole percent of ε-caprolactone, trimethylene carbonate or ether lactone repeating units in these polymers should be in the range of from about 65 to about 35 mole percent and preferably in the range of from 40 to 60 mole percent. Most preferably these liquid polymers will be statistically random copolymers.

The liquid polymers of this invention are characterized by being liquids at room temperature (25° C.) in the absence of solvents or the like. These liquid copolymers should have an inherent viscosity as determined in a 0.10 g/dL solution of hexafluoroisopropanol (HFIP) at 25° C. ranging from about 0.05 dL/g to about 0.5 dL/g, preferably from about 0.05 dL/g to about 0.3 dL/g, and most preferably from 0.1 dL/g to 0.2 dL/g. A liquid copolymer with an inherent viscosity below 0.05 dL/g may be slightly soluble in body fluids, and a liquid copolymer with an inherent viscosity above 0.5 dL/g may be too viscous to be easily injected.

These polymers may be formed in a ring opening polymerization reaction. Currently, it is preferred to initiate the ring opening polymerization with high boiling alcohols (such as 1-dodecanol), diols and triols (such as 1,2-propanediol, 1,3-propanediol, diethylene glycol, or glycerol) or polyols (such as polyethyleneglycols or polypropyleneglycols). Additionally, some of the monomers described above may be replaced by an equivalent amount of the corresponding acid (such as the substitution of two equivalents of glycolic acid for glycolide or two equivalents of L-lactic acid for L-lactide).

The liquid copolymers may contain varying amounts of the different copolymers depending on the specific properties that the liquid copolymer is desired to have.

The viscosity of the liquid copolymers may also vary depending on the molecular weights of the liquid copolymers as well as on the composition of the polymers used as the liquid. Generally, the viscosity of the liquid copolymers will be less than 10,000 poise and preferably will be in the range of from about 20 poise to about 2,000 poise as determined by capillary rheometry.

The injectable liquid copolymers can be used for a variety of soft tissue repair and augmentation procedures. For example, the liquid polymers can be used in facial tissue repair or augmentation including but not limited to camouflaging scars, filling depressions, smoothing out irregularity, correcting asymmetry in facial hemiatrophy, second branchial arch syndrome, facial lipodystrophy and camouflaging age-related wrinkles as well as augmenting facial eminences (lips, brow, etc.). Additionally, these injectable liquid polymers can be used to restore or improve sphincter function such as for treating stress urinary incontinence. Other uses of these injectable liquid polymers may also include the treatment of vesicoureteral reflux (incomplete function of the inlet of the ureter in children) by subureteric injection and the application of these liquid polymers as general purpose fillers in the human body.

Surgical applications for injectable, biodegradable liquid polymers include, but are not limited to: facial contouring (frown or glabellar line, acne scars, cheek depressions, vertical or perioral lip lines, marionette lines or oral commissures, worry or forehead lines, crow's feet or periorbital lines, deep smile lines or nasolabial folds, smile lines, facial scars, lips and the like); periurethral injection including injection into the submucosa of the urethra along the urethra, at or around the urethral-bladder junction to the external sphincter; ureteral injection for the prevention of urinary reflux; injection into the tissues of the gastrointestinal tract for the bulking of tissue to prevent reflux; to aid in sphincter muscle coaptation, internal or external, and for coaptation of an enlarged lumen; intraocular injection for the replacement of vitreous fluid or maintenance of intraocular pressure for retinal detachment; injection into anatomical ducts to temporarily plug the outlet to prevent reflux or infection propagation; larynx rehabilitation after surgery or atrophy; and any other soft tissue which can be augmented for cosmetic or therapeutic affect. Surgical specialists which would use such a product include, but are not limited to, plastic and reconstructive surgeons; dermatologists; facial plastic surgeons, cosmetic surgeons, otolaryngologists; urologists; gynecologists; gastroenterologists; ophthalmologists; and any other physician qualified to utilize such a product.

Additionally, to facilitate the administration and treatment of patients with the inventive liquid copolymer, pharmaceutically active compounds or adjuvants can be administered therewith. The pharmaceutically active agents that may be coadministered with the inventive liquid polymers include but ate not limited to anesthetics (such as lidocaine) and antiinflammatories (such as cortisone).

The liquid copolymers can be administered with a syringe and needle or a variety of devices. Several delivery devices have been developed and described in the art to administer viscous liquids such as the carpule devices described by Dr. Orentriech in U.S. Pat. Nos. 4,664,655 and 4,758,234 which are hereby incorporated by reference. Additionally, to make delivery of the liquid copolymer as easy as possible for the doctors, a leveraged injection rachet mechanism or powered deliver mechanism may be used. It is currently preferred for the liquid polymers to be preloaded in a cylindrical container or cartridge having two ends. The first end would be adapted to receive a plunger and would have a movable seal placed therein. The second end or outlet would be covered by a removable seal and be adapted to fit into a needle housing to allow the liquid copolymers in the container to exit the outlet and enter a needle or other hollow tubular member of the administration device. It is also envisioned that the liquid copolymers could be sold in the form of a kit comprising a device containing the liquid copolymers. The device having an outlet for said liquid copolymers, an ejector for expelling the liquid copolymers and a hollow tubular member fitted to the outlet for administering the liquid copolymers into an animal.

The following nonlimiting examples are provided to further illustrate the practice of the present invention.

EXAMPLES

Example 1

LIQUID POLYMERS OF ε-CAPROLACTONE/L-LACTIDE AT 50/50 INITIAL MOLE COMPOSITION

A flame dried, 250 mL, round bottom single neck flask was charged with 57.1 grams (0.50 mole) of ε-caprolactone, 72.1 grams (0.50 mole) of L-lactide, 4.00 mL (55 mmol) of distilled glycerol, and 0.10 mL (34 pmol) of a 0.33M stannous octoate solution in toluene. The flask was fitted with a flame dried mechanical stirrer. The reactor was purged with nitrogen three times before venting with nitrogen. The reaction mixture was heated to 160° C. and maintained at this temperature for about 18–20 hours. The copolymer was dried under vacuum (0.1 mm Hg) at 110° C. for about 16 hours to remove any unreacted monomer. The copolymer had an inherent viscosity of 0.14 dL/g in hexafluoroisoproponal (HFIP) at 25° C. The copolymer was a liquid at room temperature. The molar ratio of PCL/PLA was found to be 53.7/46.3 by proton NMR.

Example 2

LIQUID POLYMERS OF ε-CAPROLACTONE/L-LACTIDE AT 50/50 INITIAL MOLE COMPOSITION

The procedure in Example 1 was substantially repeated, except that 13.6 mL of 1-dodecanol instead of 4.00 mL of glycerol and 0.12 mL (40 pmol) instead of 0.10 mL of stannous octoate solution were used. The copolymer was dried under vacuum (0.1 mm Hg) at 110° C. for about 16 hours to remove any unreacted monomer. The copolymer had an inherent viscosity of 0.15 dL/g in HFIP at 25° C. The copolymer was viscous liquid at room temperature. The molar ratio of PCL/PLA was found to be 51.5/48.5 by proton NMR.

Example 3

LIQUID POLYMERS OF ε-CAPROLACTONE/L-LACTIDE AT 50/50 INITIAL MOLE COMPOSITION

The procedure in Example 2 was substantially repeated, except that 5.6 mL of 1-dodecanol was used instead of 13.6 mL. The copolymer was dried under vacuum (0.1 mm Hg) at 110° C. for about 16 hours to remove any unreacted monomer. The copolymer had an inherent viscosity of 0.28 dL/g in HFIP at 25° C. The copolymer was very a viscous liquid at room temperature. The molar ratio of PCL/PLA was found to be 50.5/49.5 by proton NMR.

Example 4

LIQUID POLYMERS OF ε-CAPROLACTONE/L-LACTIDE AT 50/50 INITIAL MOLE COMPOSITION

The procedure in Example 3 was substantially repeated, except that 4.4 mL (60 mmol) propylene glycol (USP grade) was used instead of 5.6 mL of 1-dodecanol. The copolymer had an inherent viscosity of 0.17 dL/g in HFIP at 25° C.

Example 5A

LIQUID POLYMERS OF C-CAPROLACTONE/p-DIOXANONE AT 50/50 INITIAL MOLE COMPOSITION

A flame dried, 250 mL, round bottom single neck flask was charged with 57.1 grams (0.50 mole) of ε-caprolactone, 51.0 grams (0.50 mole) of p-dioxanone, 4.00 mL (55 mmol) of distilled glycerol, and 0.12 mL (40 pmol) of a 0.33M stannous octoate solution in toluene. The flask was fitted with a flame dried mechanical stirrer. The flask was purged with nitrogen three times before venting with nitrogen. The reaction mixture was heated to 140° C. and maintained at this temperature for about 24 hours. The reaction mixture was then cooled to 110° C. and maintained at this temperature for 24 hours. The copolymer was dried under vacuum (0.1 mm Hg) at 80° C. for about 32 hours to remove any unreacted monomer. The copolymer had an inherent viscosity of 0.14 dL/g in HFIP at 25° C. The copolymer was a liquid at room temperature. The molar ratio of PCL/PDS was found to be 53.2/46.8 by proton NMR.

Example 5B

LIQUID POLYMERS OF ε-CAPROLACTONE/p-DIOXANONE AT 50/50 INITIAL MOLE COMPOSITION

A flame dried, 250 mL, round bottom single neck flask was charged with 57.1 g (0.50 mole) of ε-caprolactone, 51.0 grams (0.50 mole) of p-dioxanone, 3.7 mL (50 mmol) of propylene glycol (USP), and 0.12 mL (34 pmol) of a 0.33M stannous octoate solution in toluene. The flask was fitted with a flame dried mechanical stirrer. The flask was purged with nitrogen three times before venting with nitrogen. The reaction mixture was heated to 140° C. and maintained at this temperature for about 24 hours and then bath temperature was lowered to 110° C. and maintained at this temperature for 24 hours. The copolymer was dried under vacuum (0.1 mm Hg) at 80° C. for about 32 hours to remove any unreacted monomer. The copolymer had an inherent viscosity of 0.22 dL/g in HFIP at 25° C. The copolymer was a liquid at room temperature. The molar ratio of PCL/PDS was found to be 52.4/47.6 by proton NMR.

Example 5C

LIQUID POLYMERS OF ε-CAPROLACTONE/p-DIOXANONE AT 60/40 INITIAL MOLE COMPOSITION

The procedure in Example 5A was substantially repeated, except that 68.48 grams (0.60 mole) of ε-caprolactone and 40.83 grams (0.40 mole) of p-dioxanone were used. The copolymer was dried under vacuum (0.1 mm Hg) at 80° C. for about 80 hours to remove any unreacted monomer. The copolymer had an inherent viscosity of 0.19 dL/g in HFIP at 25° C. The copolymer was a liquid at room temperature. The molar ratio of PCL/PDS was found to be 57.2/42.8 by proton NMR.

Example 5D

LIQUID POLYMERS OF ε-CAPROLACTONE/p-DIOXANONE AT 40/60 INITIAL MOLE COMPOSITION

The procedure in Example 5A is substantially repeated except that 45.7 grams (0.40 mole) of ε-caprolactone and 61.3 grams (0.60 mole) of p-dioxanone were used. The copolymer was dried under vacuum (0.1 mm Hg) at 80° C. for about 80 hours to remove any unreacted monomer. The copolymer had an inherent viscosity of 0.18 dL/g in HFIP at 25° C. The copolymer was a liquid at room temperature. The molar ratio of PCL/PDS was found to be 46.7/53.3 by proton NMR.

Example 6

LIQUID POLYMERS OF ε-CAPROLACTONE/p-DIOXANONE AT 50/50 INITIAL MOLE COMPOSITION

The procedure in Example 5A was substantially repeated except that 13.6 mL 1-dodecanol was used instead of 4.00 mL of glycerol. The copolymer was dried under vacuum (0.1 mm Hg) at 80° C. for about 32 hours to remove any unreacted monomer. The copolymer had an inherent viscosity of 0.16 dL/g in HFIP at 25° C. The copolymer was a liquid at room temperature.

Example 7

LIQUID POLYMERS OF ε-CAPROLACTONE/p-DIOXANONE AT 50/50 INITIAL MOLE COMPOSITION

The procedure in Example 5A was substantially repeated except that 6.8 mL instead of 13.6 mL 1-dodecanol was used. The copolymer was dried under vacuum (0.1 mm Hg) at 80° C. for about 16 hours to remove any unreacted monomer. The copolymer had an inherent viscosity of 0.24 dL/g in HFIP at 25° C. The copolymer was a viscous liquid at room temperature. The molar ratio of PCL/PDS was found to be 53.6/46.4 by proton NMR.

Example 8

LIQUID POLYMERS OF ε-CAPROLACTONE/p-DIOXANONE AT 50/50 INITIAL MOLE COMPOSITION

The procedure in Example 7 was substantially repeated except that 4.4 mL (60 mmol) of propylene glycol (USP) was used instead of 6.8 mL of 1-dodecanol. The copolymer was dried under vacuum (0.1 mm Hg) at 80° C. for about 16 hours to remove any unreacted monomer. The copolymer had an inherent viscosity of 0.17 dL/g in HFIP at 25° C. The copolymer was a viscous liquid at room temperature.

Example 9

LIQUID POLYMERS OF ε-CAPROLACTONE/ TRIMETRYLENE CARBONATE AT 50/50 INITIAL MOLE COMPOSITION

A flame dried, 250 mL, round bottom single neck flask was charged with 57.1 grams (0.50 mole) of ε-caprolactone, 51.0 grams (0.50 mole) of trimethylene carbonate, 4.4 mL (60 mmol) of propylene glycol (USP), and 0.10 mL (34 Mmol) of a 0.33M solution of stannous octoate in toluene. The flask was fitted with a flame dried mechanical stirrer. The flask was purged with nitrogen three times before venting with nitrogen. The reaction mixture was heated to 160° C. and maintained at this temperature for about 18–20 hours. The copolymer was dried under vacuum (0.1 mm Hg) at 80° C. for about 16 hours to remove any unreacted monomer. The copolymer had an inherent viscosity of 0.20 dL/g in HFIP at 25° C. The copolymer was a viscous liquid at room temperature.

Example 10

LIQUID POLYMERS OF ε-CAPROLACTONE/ TRIMETHYLENE CARBONATE AT 90/10 INITIAL ROLE COMPOSITION

A flame dried, 250 mL, round bottom single neck flask was charged with 102.7 grams (0.90 mole) of ε-caprolactone, 10.2 grams (0.10 mole) of trimethylene carbonate, 2.9 mL (40 mmol) of propylene glycol (USP), and 0.10 mL (34 pmol) of a 0.33M stannous octoate solution in toluene. The flask was fitted with a flame dried mechanical stirrer. The flask was purged with nitrogen three times before venting with nitrogen. The reaction mixture was heated to 160° C. and maintained at this temperature for about 18–20 hours. The copolymer was dried under vacuum (0.1 mm Hg) at 80° C. for about 16 hours to remove any unreacted monomer. The copolymer had an inherent viscosity of 0.25 dL/g in HFIP at 25° C. The copolymer was a viscous liquid at room temperature.

Example 11

VISCOSITY OF LIQUID ABSORBABLE COPOLYMERS

This example presents viscosity data on liquid absorbable polymers which were prepared in a manner similar to that described in Examples 1–9.

The viscosity of the polymers were determined by capillary rheometry. The viscosity data for the liquid absorbable polymers are presented in Tables 1, 2, and 3.

TABLE 1

Viscosity Data on Liquid Absorbable Copolymer of ε-Caprolactone and p-Dioxanone

| Sample No. | Copolymer Composition in Mole Percents[1] | | Inherent Viscosity[2] (dL/g) | Viscosity in Poise | |
|---|---|---|---|---|---|
| | ε-Caprolactone | p-Dioxanone | | @ 37° C. | @ 23° C. |
| 1 | 50 | 50 | 0.08 | 16 | 43 |
| 2 | 50 | 50 | 0.09 | 12 | 34 |
| 3 | 50 | 50 | 0.14 | 32 | 86 |
| 4 | 50 | 50 | 0.14 | 16 | 37 |
| 5 | 50 | 50 | 0.16 | 22 | 49 |
| 6 | 50 | 50 | 0.17 | 31 | 78 |
| 7 | 50 | 50 | 0.22 | 92 | 255 |
| 8 | 50 | 50 | 0.24 | 106 | 279 |
| 9 | 60 | 40 | 0.14 | 20 | 51 |
| 10 | 60 | 40 | 0.14 | 19 | 45 |
| 11 | 60 | 40 | 0.15 | 20 | 47 |
| 12 | 70 | 30 | 0.16 | 18 | 42 |
| 13 | 70 | 30 | 0.16 | 15 | 32 |
| 14 | 70 | 30 | 0.16 | 15 | 35 |

[1]Based on the initial composition in the polymerization reaction.
[2]The inherent viscosity was determined in a 0.1 dL/g solution of HFIP at 25° C.

TABLE 2

Viscosity Data on Liquid Absorbable Copolymers 50:50 (mol/mol) Poly[ε-Caprolactone-co-L-Lactide][1]

| Sample No. | Inherent Viscosity[2] (dL/g) | Viscosity in Poise | |
|---|---|---|---|
| | | @ 37° C. | @ 23° C. |
| 1 | 0.06 | 49 | 216 |
| 2 | 0.08 | 98 | 461 |
| 3 | 0.09 | 102 | 442 |
| 4 | 0.09 | 93 | 396 |
| 5 | 0.12 | 179 | 919 |
| 6 | 0.14 | 370 | 1,985 |
| 7 | 0.15 | 377 | 1,786 |
| 8 | 0.13 | 193 | 901 |
| 9 | 0.14 | 198 | 945 |
| 10 | 0.17 | 317 | 1,286 |
| 11 | 0.16 | 448 | 2,344 |
| 12 | 0.17 | 892 | 5,407 |
| 13 | 0.28 | 4,903 | 23,004 |

[1]Based on the initial composition in the polymerization reaction.
[2]The inherent viscosity was determined in a 0.1 dL/g solution of HFIP at 25° C.

TABLE 3

Viscosity Data on Liquid Absorbable Polymers 50:50 (mol/mol) Poly[ε-caprolactone-co-trimethylene carbonate][1]

| Sample No. | Inherent Viscosity[2] (dL/g) | Viscosity in Poise | |
|---|---|---|---|
| | | @ 37° C. | @ 23° C. |
| 1 | 0.2 | 87 | 216 |
| 2 | 0.18 | 69 | 178 |
| 3 | 0.13 | 42 | 106 |
| 4 | 0.16 | 37.6 | 102.4 |
| 5 | 0.16 | 41.1 | 105.0 |
| 6 | 0.14 | 32.5 | 86.6 |
| 7 | 0.14 | 34.0 | 90.1 |
| 8 | 0.13 | 23.7 | 60.6 |
| 9 | 0.13 | 20.2 | 51.5 |
| 10 | 0.13 | 21.1 | 54.9 |
| 11 | 0.13 | 27.2 | 69.4 |
| 12 | 0.14 | 47.7 | 120.4 |
| 13 | 0.15 | 43.8 | 110.4 |
| 14 | 0.13 | 29.3 | 72.9 |

TABLE 3-continued

Viscosity Data on Liquid Absorbable Polymers
50:50 (mol/mol) Poly[ε-caprolactone-co-trimethylene carbonate][1]

| Sample No. | Inherent Viscosity[2] (dL/g) | Viscosity in Poise @ 37° C. | Viscosity in Poise @ 23° C. |
|---|---|---|---|
| 15 | 0.13 | 27.5 | 69.1 |
| 16 | 0.15 | 49.9 | 127.5 |
| 17 | 0.14 | 33.8 | 84.3 |
| 18 | 0.14 | 35.1 | 87.4 |
| 19 | 0.14 | 34.8 | 85.8 |
| 20 | 0.13 | 35.8 | 89.0 |
| 21 | 0.1 | 17.3 | 41.6 |
| 22 | 0.09 | 8.0 | 17.8 |
| 23 | 0.15 | 44.6 | 114.0 |

[1]Based on the initial composition in the polymerization reaction.
[2]The inherent viscosity was determined in a 0.1 dL/g solution of HFIP at 25° C.

Example 12

POLY(L-LACTIC ACID) OLIGOMERS

Poly(L-lactic acid) oligomers were prepared as described in Example 1 of German Patent Application DE 4,235,312 Al. For instance, 100.0 grams (0.94 mol) of an 85 weight percent solution of L-lactic acid was transferred into a clean, three neck, 250 mL round bottom flask equipped with a mechanical stirrer, a distillation head, and a stopper. The reaction vessel was evacuated using an aspirator (ca. 25 mm Hg) and then heated with an oil bath to 150° C. for five hours. 22 mL (1.2 mol) of water were collected. The hot poly(L-lactic acid) oligomer (A) was poured into a wide mouth jar and allowed to cool down to room temperature under a nitrogen gas atmosphere. The oligomer (A) was a highly viscous liquid having an inherent viscosity of 0.06 dL/g in HFIP at 25° C. The melt viscosity of oligomer (A) was measured on a Rheometries RDA II viscometer and was found to be 18,000 poise and Newtonian in nature at 25° C.

The above procedure was repeated except that the reaction time was increased to 24 hours. 25 mL of water were collected. The resulting oligomer (B) was a crystalline solid with a melting point range between 75° C. and 83° C. as measured on a Fisher-Johns melting point apparatus. The inherent viscosity of oligomer (B) was 0.15 dL/g in HFIP at 25° C.

A 50:50 (w/w) blend of oligomer (A) and oligomer (B) was made by transferring 20.0 grams of each oligomer into a 250 mL round bottom flask equipped with a mechanical stirrer and an adaptor with a port connected to a stream of dry nitrogen gas and a Firestone valve via tygon tubing. This mixture was heated to 160° C. for thirty minutes, transferred into a wide mouth jar, and allowed to cool down to room temperature in an inert atmosphere. The blend was a transparent, stiff material having an inherent viscosity of 0.08 dL/g in HFIP at 25° C. The blend was, in fact, a very viscous fluid at room temperature as demonstrated by its slow flow through a tube overnight. After standing at room temperature for five weeks in a jar, the bulk of the blend was still transparent; only the surface layer was translucent.

We claim:

1. A method for repairing or augmenting soft tissue in animals comprising the steps of:
   selecting the animal soft tissue to be repaired or augmented and
   placing into the animal's soft tissue an injectable, bioabsorbable liquid copolymer suitable for use as a soft tissue repair or augmentation material composed of a liquid copolymer selected from the group consisting of liquid polymers composed of a plurality of at least two different first lactone repeating units and liquid polymers of a plurality of first lactone and second lactone repeating units; wherein the first lactone repeating units are selected from the group consisting of ε-caprolactone repeating units, trimethylene carbonate repeating units, ether lactone repeating units and combinations thereof; and the second lactone repeating units are selected from the group consisting of glycolide repeating units, p-dioxanone repeating units and combinations thereof; wherein the liquid copolymers are liquids at room temperature (25° C.).

2. The method of claim 1 wherein the liquid copolymer selected from the group consisting of polymers of from about 65 mole percent to about 35 mole percent of ε-caprolactone repeating units with the remainder being the second lactone group of repeating units, polymers of from about 65 to about 35 mole percent of ether lactone repeating units with the remainder being second lactone group of repeating units, polymers of from about 65 to about 35 mole percent of trimethylene carbonate repeating units with the remainder being second lactone group of repeating units, polymers of from about 65 mole percent to about 35 mole percent of ε-caprolactone repeating units with the remainder of the polymer being trimethylene carbonate repeating units, and polymers of from about 65 to about 35 mole percent ether lactone repeating units with the remainder being trimethylene carbonate repeating units.

3. The method of claim 2 wherein the liquid polymer is selected from the group consisting of poly(e-caprolactone-co-trimethylene carbonate), poly(e-caprolactone-co-p-dioxanone), poly(trimethylene carbonate-co-p-dioxanone), poly(1,4-dioxepan-2-one-co-p-dioxanone), and poly(1,5-dioxepan-2-one-co-p-dioxanone).

4. The method of claim 2 wherein the animal soft tissue selected is the skin.

5. The method of claim 2 wherein the liquid polymer is injected into facial soft tissue to provide facial contouring.

6. The method of claim 2 wherein the animal soft tissue selected is a sphincter muscle.

7. The method of claim 2 wherein the animal soft tissue selected is the urinary bladder.

8. The method of claim 1 wherein the liquid copolymer is used for a procedure to repair or augment facial tissue selected from the group consisting of camouflaging scars, filling depressions, smoothing out irregularities, correcting asymmetry in facial hemiatrophy, second bronchial arch syndrome, facial lipodystrophy, camouflaging wrinkles and augmenting facial eminences.

9. The method of claim 1 wherein the liquid copolymer is injected to treat urinary incontinence.

10. The method of claim 1 wherein the liquid copolymer is injected to treat vesicoureteral reflux.

11. A method for repairing or augmenting soft tissue in animals comprising the steps of:
    selecting the animal soft tissue to be repaired or augmented and
    placing into the animal's soft tissue an injectable, bioabsorbable liquid copolymer suitable for use as a soft tissue repair or augmentation material composed of a liquid copolymer selected from the group consisting of liquid polymers composed of a plurality of at least two different first lactone repeating units and liquid polymers of a plurality of first lactone and second lactone repeating units; wherein the first lactone repeating units are selected from the group consisting of, trimethylene carbonate repeating units, ether lactone repeating units and combinations thereof; and the second lactone repeating units are selected from the group consisting of glycolide repeating units, lactide repeating units, p-dioxanone repeating units and combinations thereof; wherein the liquid copolymers are liquids at room temperature (25° C.).

12. The method of claim 11 wherein the liquid copolymer selected from the group consisting polymers of from about 65 to about 35 mole percent of ether lactone repeating units with the remainder being second lactone group of repeating units, and polymers of from about 65 to about 35 mole percent of trimethylene carbonate repeating units with the remainder being second lactone group of repeating units.

13. The method of claim 11 wherein the liquid polymer is selected from the group consisting poly(lactide-co-trimethylene carbonate), poly(lactide-co-1,4-dioxepan-2-one), and poly(lactide-co-1,5-dioxepan-2-one).

14. The method of claim 11 wherein the animal soft tissue selected is the skin.

15. The method of claim 11 wherein the liquid polymer is injected into facial soft tissue to provide facial contouring.

16. The method of claim 11 wherein the liquid copolymer is used for a procedure to repair or augment facial tissue selected from the group consisting of camouflaging scars, filling depressions, smoothing out irregularities, correcting asymmetry in facial hemiatrophy, second bronchial arch syndrome, facial lipodystrophy, camouflaging wrinkles and augmenting facial eminences.

17. The method of claim 11 wherein the animal soft tissue selected is a sphincter muscle.

18. The method of claim 11 wherein the animal soft tissue selected is the urinary bladder.

19. The method of claim 11 wherein the liquid copolymer is injected to treat urinary incontinence.

20. The method of claim 11 wherein the liquid copolymer is injected to treat vesicoureteral reflux.

* * * * *